United States Patent [19]

Reim et al.

[11] 4,010,857
[45] Mar. 8, 1977

[54] COAL CONDITIONING SYSTEM

[75] Inventors: Thomas E. Reim, Willowick; Jerry J. Pollack, Brookpark; Robert A. Kemmerling, Cleveland, all of Ohio

[73] Assignee: Republic Steel Corporation, Cleveland, Ohio

[22] Filed: Oct. 29, 1970

[21] Appl. No.: 85,238

Related U.S. Application Data

[62] Division of Ser. No. 720,057, April 10, 1968, abandoned.

[52] U.S. Cl. ............................ 214/18 R; 100/74; 100/144; 198/339; 198/607
[51] Int. Cl.² .................................. F23K 3/00
[58] Field of Search .................. 75/3-5; 198/40, 39, 82, 102; 214/18 R; 250/308, 354, 358-360; 100/70 R, 71, 73-75, 95, 97, 144, 192

[56] References Cited

UNITED STATES PATENTS

| 1,750,839 | 3/1930 | Furbush | 198/102 |
| 3,148,971 | 9/1964 | MacDonald | 75/5 |

FOREIGN PATENTS OR APPLICATIONS

| 983,334 | 2/1965 | United Kingdom | 198/39 |

Primary Examiner—Evon C. Blunk
Assistant Examiner—Joseph E. Valenza
Attorney, Agent, or Firm—Cooper, Dunham, Clark, Griffin & Moran

[57] ABSTRACT

The output of a radioactive source is directed through a moving stream of granular material, e.g., coal on a conveyor, and the radiation passing through is sensed by a detector. The detector generates a pulse signal of which the pulse repetition rate varies with the radiation sensed. The pulses generated are counted in a binary counter, and a timer periodically initiates a read-out of and resets the counter to effect successive counting cycles, whereupon the digital count in each cycle is converted to an analog voltage, the magnitude of which is recorded in terms of bulk density of the coal. The recorder controls the addition of water or oil to the coal to, respectively, lower or increase the bulk density of the coal. Controls are included which guard the system from misperforming when a supply of coal has failed, when the depth of coal on the conveyor belt has been lost, and when the coal is so dense that an application of water is required.

The system employs a drop of the coal before it passes the source of radiation so as to simulate the drop of coal in an oven to which the coal is normally supplied, thereby to present coal for bulk density control in a condition the same as that applied to the oven. A paddle-wheel assembly may be employed for this same purpose by striking the material as it is dropped past the paddle-wheel assembly. Alternatively, a sled assembly that tamps the coal may be employed for such simulation.

9 Claims, 5 Drawing Figures

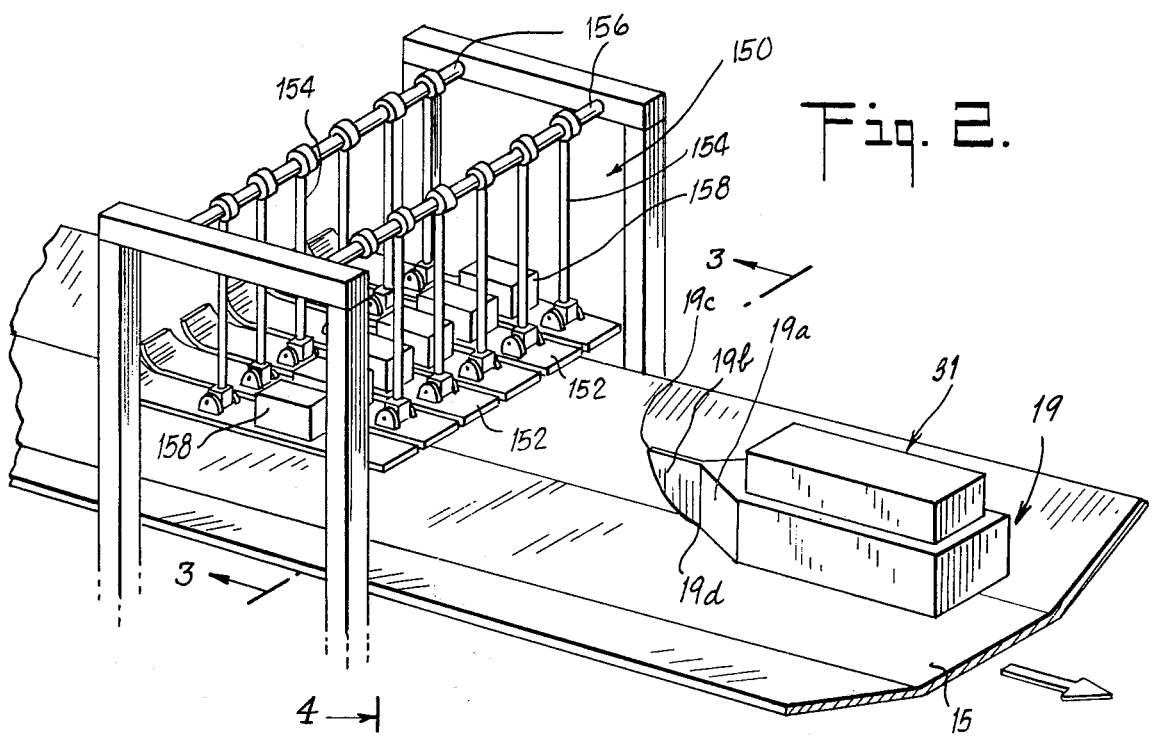
Fig. 2.
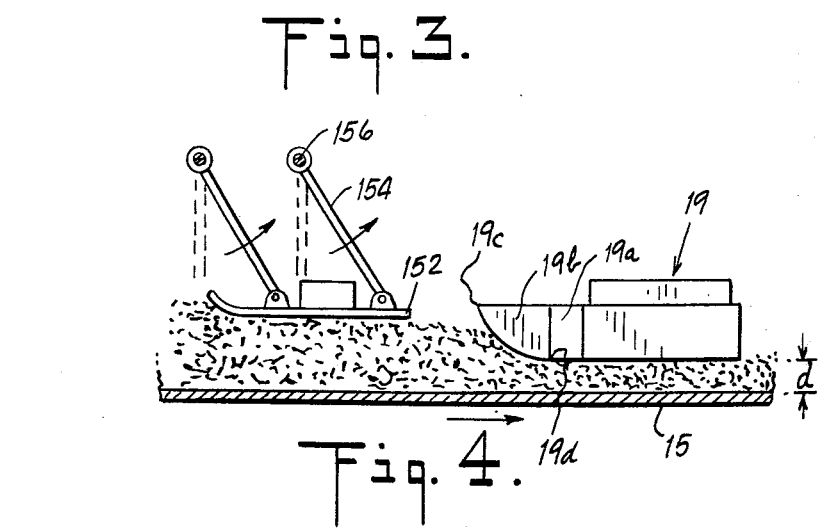
Fig. 3.
Fig. 4.

COAL CONDITIONING SYSTEM

CROSS REFERENCE TO RELATED APPLICATION

This application is a division of our copending Application Ser. No. 720,057, filed Apr. 10, 1968, for "Bulk Density Gage and Bulk Density Control System." That application number 720,057 is now abandoned; the continuation of that abandoned application is Ser. No. 87,360 filed 5 November 1970 and which issued as U.S. Pat. No. 3,678,268.

BACKGROUND OF THE INVENTION

This invention relates to a method and apparatus for measuring and controlling the bulk density of granular material. It has particular application to the measurement and control of the bulk density of coal in a coke oven charging system. Bulk density variations in coking coals has been a problem primarily because of variations in the surface moisture of the coal. As surface moisture increases, and the coal is mixed or handled, the bulk density decreases with a corresponding volume increase. As the surface moisture decreases, and the coal is mixed or handled, the bulk density increases with a corresponding volume decrease. It is now generally recognized that one of the most important factors affecting the uniformity of coke oven operations and the quality and quantity of coke produced is the bulk density of coal that is charged into the coke oven. Changes in the bulk density of the coal away from an optimum density not only cause irregularity in coke oven heating and in oven pressure, which are reflected in impaired quality of the coke; but it also causes variations in the oven output adversely affecting the coke yield.

It is known that the addition of a small amount of oil to the granular coking coal will significantly increase its bulk density and that the addition of water will significantly lower its bulk density. Accordingly, various methods and devices have been used with rather poor success to control the bulk density of the coking coal by adding varying amounts of oil and/or water in order to obtain and maintain the coal within an optimum bulk density range which has been determined as the range which will yield the greatest quantity of high quality coke without danger of damage to the brick work of the coke oven.

Heretofore, there has been no satisfactory way in which the bulk density of coal could be gaged on a continuous basis to provide a criterion for the automatic addition of water and/or oil to adjust and maintain the bulk density of the coal within a predetermined density range.

Initially the measurement and control of bulk density of the coal was by resort to batch sampling and manually controlled water and/or oil additions, according to which samples of coal removed from a moving conveyor belt were subjected to a laboratory volume weight bulk density test at a remote point. This method of obtaining the bulk density of coking coal is time consuming and substantial amounts of coal are charged into the oven before any correction in the bulk density can be made by adding oil or water. Further, this method does not provide accurate bulk density determination or control. It is vital to obtain accurate gaging that the coal be subjected to the handling it gets when charged into the oven. A vital part of the present system is to simulate this condition prior to gaging by allowing coal to fall the correct distance or to simulate such fall.

A continuous weight-type test for bulk density has also been suggested. According to the latter proposal, a continuous sample stream of coal is diverted from a main flow onto a fixed speed conveyor used to deliver a constant volume of coal over a weight belt to produce a weight signal which is converted into a bulk density reading. Signals from this system have been instrumented to record bulk density and to automatically control water and oil additions to produce a desired bulk density. This system has had the disadvantage, as have all the sampling techniques, of the bulk density measurement being made on a comparatively small sample, wherein the sample bulk density has often varied from the bulk density of the coal actually charged into the coke oven. Moreover, this system requires additional chutes, hoppers, bins, belts and conveyors which add to the cost and complexity of the required equipment.

It has been proposed in the past to automatically detect the bulk density of coal by directing radiation to the coal as it passes a detecting station, and utilizing the detected radiation to control the addition of oil and water to vary the bulk density of the coal. Macdonald et al U.S. Pat. No. 3,148,971 discloses such a system. This patent does not go into the details of the radiation detector nor the control system, but simply indicates that water and oil rates are increased or decreased in accordance with detected changes in bulk density. In a system to be workable, however, it is not sufficient simply to increase or decrease the rates of water and oil addition. It has been found in the present invention that one of the two fluid components should be varied with respect to the other. Generally the rate of oil addition is considered to be the primary control in the present invention, and the water addition rate is varied not only in accordance with bulk density but also in accordance with the rate of oil addition so as to optimize the control of bulk density. Additionally, it has been found in the present invention desirable to employ digital pulse counting techniques in the detection and control of the bulk density of a granular material. Although digital pulse counting techniques have been employed in the past (see, for example, Willett et al U.S. Pat. No. 3,136,892 directed to the detection of heart rot in power line poles), the present invention utilizes such techniques in bulk density control and in a novel way to ensure control of a process over a predetermined range of counts representing a permissible range of bulk densities over which control is to take place.

It is an object of this invention, therefore, to provide an improved means for accurately, continuously, automatically and economically measuring and maintaining a uniform predetermined bulk density of granular material such as coal charged into a coke oven, which eliminates the above-mentioned disadvantages.

BRIEF DESCRIPTION OF THE INVENTION

This invention contemplates a radioactive source for directing radiation through a moving stream of granular material, e.g., coal, and a radiation detector for measuring the amount of radiation passing through the material. In one embodiment, this invention comprises a plow for leveling coal on a belt carrying the coal to a coke oven, a radioactive radiation source for directing radiation through the coal so leveled, detecting means for receiving radiation passing through the coal, means for determining the bulk density of the coal as a function of the detected radiation, means for indicating and recording the bulk density, and means operable with the indicating and recording means for controlling the addition of water and oil to the coal to change the bulk density of the coal to a desired bulk density.

The invention contemplates dropping the coal by a distance substantially the same as the distance it falls in the coke ovens. This is done before the radiation is directed to the coal so that the coal will be in a condition substantially the same as that in the coke ovens. If it is not advantageous to drop the coal by this distance, different arrangements are proposed herein to make the bulk density the same as in the ovens. One is a sled assembly which bears against the coal, and another is a paddle-wheel assembly which strikes the coal as it is made to fall from one point to another.

Further, the addition of oil and water in the present invention, as noted above, is achieved within a range of permissible bulk densities. As the bulk density varies within the range and outside of the range, changes are made in the addition of oil and water. Straightforward control of water and oiling rates in accordance with detected bulk density is employed, as well as special control of water rate in accordance with oiling rate. Further, safety features to discontinue addition of oil and/or water and oil in the event of a loss of coal are also utilized.

The above and further objectives and novel features of the invention will appear more fully in the following detailed description when the same is read in connection with the accompanying drawings. It is to be expressly understood, however, that the drawings are not intended as a definition of the invention but are for the purpose of illustration only.

BRIEF DESCRIPTION OF THE DRAWINGS

In the drawings, like reference numerals indicate like parts, and

FIG. 2 is a perspective view of a sled assembly for varying the bulk density of coal to simulate a drop in an oven and a plow for mounting a source of radiation, all in accordance with the invention;

FIG. 3 is a sectional view of the apparatus shown in FIG. 2, taken along the section line 3—3 of FIG. 2;

FIG. 4 is a sectional view of the apparatus of FIG. 3, taken along section line 4—4 of FIG. 3.

DETAILED DESCRIPTION

Figure 1:
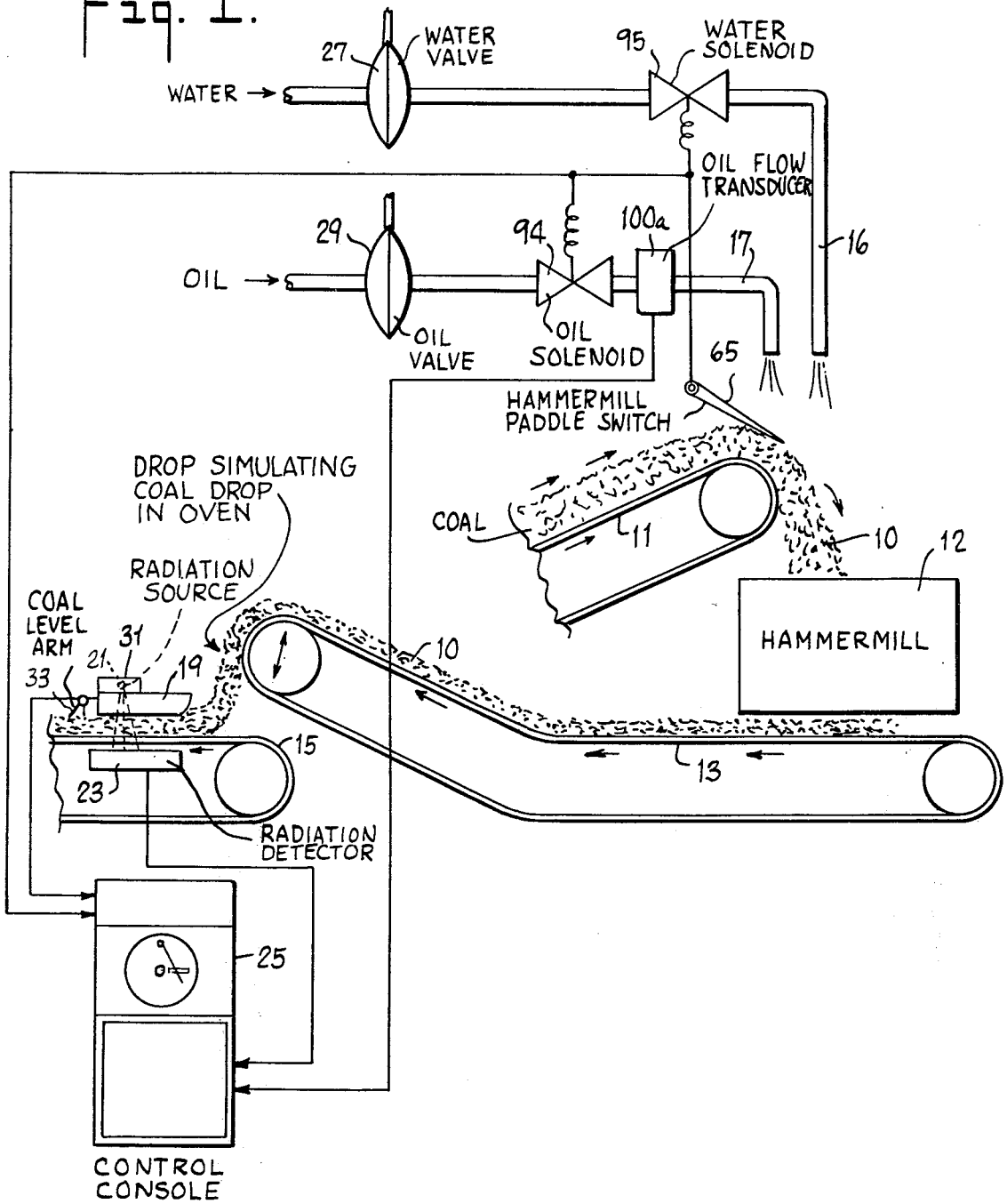
FIG. 1 is a generalized diagrammatic view of principal components of the system intended to illustrate its basic purpose and operation.

A familiarity with the essential features of the invention can be obtained by reference to FIG. 1 in which the invention has been diagrammatically shown as incorporated in a system for handling coal prior to charging the coal into a coke oven battery. The coal is received at the coke battery site as it comes directly from a mine, storage bins, or a stockyard. A mixture of different coals 10 is delivered on a conveyor belt 11 to a conventional hammermill 12 which crushes the coal and reduces it to a relatively uniform particle coal size. Thereafter, in the particular coal handling system shown, a conveyor 13 transports the coal to and drops it onto a conveyor belt 15 which carries it to the coking ovens.

To achieve a desired operation of the coke oven battery, the coal stream 10 must be maintained at a substantially uniform desired bulk density. Usually, the bulk density desired is the maximum bulk density consistent with safe oven pressures and is normally a bulk density above the minimum density that can be achieved by addition of water to the coal used. The coal received at the hammermill 12 varies widely in bulk density and the bulk density is changed at that point to a desired uniform level by the addition to the coal of small amounts of water from a pipe 16 to decrease the bulk density within certain limits, and oil from a pipe 17 to increase the bulk density within certain limits.

To measure and control the bulk density of the coal stream 10, in accordance with one embodiment of this invention, a system is used in which the coal stream 10 is leveled and the stream of coal is reduced to a uniform thickness by a plow 19 as the conveyor 15 carries the coal forward. The bulk density of the leveled coal stream is measured, and means responsive to the measurement of the bulk density causes the selective addition of oil and water to coal to maintain the density of the coal stream 10 within a predetermined bulk density range. To this end, the coal on the belt 15 is leveled by the plow 19 to produce a level, substantially freely piled longitudinally extending coal stream. The leveling step has the result of efficiently keeping the freely piled solid material in the stream sufficiently leveled to make possible the measurement and control of the bulk density of the coal stream by means of a radioactive source and detector. The details of the plow 19 which provide a parting of the coal past the plow and a leveling of the coal without the "hanging up" of the coal on the plow and without the plow catching foreign articles such as wire and the like in the coal, will be described later in connection with FIG. 2.

Prior to the leveling of the coal, the coal is dropped from the conveyor 13 onto the conveyor 15. The height of the drop, which is adjustable by adjustment of the height of conveyor 13 over conveyor 15, is made substantially the same as the drop the coal undergoes in the coke oven. Thus the coal is presented to the plow 19 and is conditioned substantially the same as it is in the oven just prior to combustion. This coal handling procedure is important, since it has been found that effective bulk density control is impossible to achieve without conditioning the coal beforehand to simulate its condition in use. Any drops occurring at other transfer points in the conveying system up to the plow 19 have no effect, since the bulk density of the coal at any given point in the system is dependent only on the height of the last drop which the coal has undergone. Specifically, when coal falls in a drop, the particles separate thus erasing any previous drop history. Thus successive drops do not produce additive increases in bulk density. The drop provided from the conveyor 13 to the conveyor 15 just prior to plow 19 thus provides a proper conditioning of the coal at the zone in which bulk density is detected. It should be noted at this point, however, that in the event a conveying system cannot be adapted to provide a drop the same as the drop that the coal undergoes in an oven, the drop may be simulated by apparatus to be described later particularly with respect to FIG. 2 to 5.

Rays from a fixed predetermined substantially constant strength of radiation from a radioactive source 21 are directed through the level coal stream to a detector 23 on the opposite side of the coal stream and at a fixed distance from the radiation source 21. The detector 23 produces a signal proportional to the radiation passing through the coal stream, and the signal is fed to a measuring, recording and controlling means 25. The recorder-controller 25 measures the bulk density of the coal stream on the basis that the signal thereto is proportional to the bulk density of the coal stream; and the recorder-controller responds to the measurement of the bulk density to actuate valves 27 and 29 to add water and/or oil selectively to the coal fed to the hammermill 12, so as to control the bulk density of the coal stream to a predetermined substantially constant amount.

Various types of radiation sources may be used in accordance with the invention, including gamma ray emitting radioisotopes such as cesium 137 or radium. For example, the radiation source 21 may comprise a pellet of radium.

The radiation source 21 produces rays of sufficient strength to penetrate the coal stream 10 and the belt 15, so as to produce a signal from the detector 23 proportional to the radiation passing through the coal stream and the belt. A container 31 holds the source 21, the container is adjustably supported above the coal stream on the conveyor. The rays of energy from the source 21 are made to irradiate a predetermined portion of the stream.

The detector 23 is located on the side of the coal stream 10 opposite the pellet and at a fixed distance from the pellet 21, so as to receive radiation directed through the coal stream 10 and the belt 15 and to produce an electrical signal corresponding in intensity to the radiation reaching the detector 23. To this end, the detector 23 may be a plurality of GeigerMuller tubes, a scintillation counter or similar conventional apparatus.

Gamma radiation from the pellet 21 is attenuated as the radiation passes through the coal in the coal stream and through the belt and this attenuation, or absorption, is a function of the density of the material between the radiation source and the detector. Since a predetermined portion of the stream is irradiated, and since the coal leveling means 19 causes the thickness of this portion of the coal stream to be substantially constant, the absorption of the gamma rays is a function of the bulk density of the coal stream 10. Thus, the detector 23 is exposed to the variable radiation field produced by changes in the bulk density of the coal stream.

The detector 23 generates a pulse signal, the pulse repetition rate of which is representative of the bulk density of the coal within the stream. The pulse signal is acted upon in the control console 25 throughout a plurality of successive counting cycles. In particular, in each counting cycle, a predetermined range of counts is taken as representing a range of bulk densities within which control of the bulk density may be effected. As an example only, this predetermined range of counts may encompass from 1,246,208 to 1,375,232 pulses counted, representing a coal bulk density variation of from 65 to 43 pounds per cubic foot. Within this range of bulk densities a preestablished sub-range of from 43 to 53 pounds per cubic foot, for example, is considered "normal." Such a "normal" sub-range of bulk densities may be represented by a pulse count in a counting cycle falling between 1,310,720 and 1,375,232. As long as in each counting cycle the number of pulses counted falls within this preestablished sub-range, the oil and water addition rates at the hammermill 12 are varied in accordance with the count. Specifically, if a low count in a cycle is detected, representing a relatively high bulk density close to 53 pounds per cubic foot, for example, the rate of water addition is increased by suitable actuation of the water valve 27, and oil addition is decreased by actuation of valve 29. If a high count in a cycle is detected, on the other hand, representing a relatively low bulk density near 43 pounds per cubic foot, for example, the rate of oil addition is increased by actuation of the oil valve 29 and water addition is decreased.

If the pulse count falls outside of the preestablished sub-range of counts, indicating a variation of the bulk density from the "normal" range, the mode of control is changed. In the example above, the predetermined range of counts was indicated as varying from 1,246,208 to 1,375,232 pulses. This predetermined range thus encompasses the range of "normal" densities as well as other, higher bulk densities. For example, the range of bulk densities represented by pulse counts from 1,246,208 to 1,310,720 may represent a coal bulk density variation from 65 to 53 pounds per cubic foot. This is considered a relatively high bulk density, although one which lends itself to control. Accordingly, if the pulse count is within this range, the oil valve 29 is shut off, discontinuing the supply of oil to the coal. Water is increased by suitable control of the water valve 27 until either a maximum rate of water addition is achieved or until in a subsequent cycle, the bulk density returns to the "normal" range.

In the event that the pulse count is outside the predetermined range of counts, e.g., outside the range of pulse counts 1,246,208 to 1,375,232, an abnormal condition is considered to exist and all water and oil additions are discontinued.

A coal level arm 33 is mounted on the rear of the plow 19 and senses the proper level of coal in the stream 10 on the conveyor 15, sending a signal to the control circuits 25 if the proper level is lost. If the proper coal level is lost at the coal level arm, the oil flow to the coal from the pipe 17 is discontinued as by suitable actuation of the oil valve 29. Similarly, a hammermill paddle switch 65 positioned just in front of the hammermill 10 detects the application of coal to the hammermill. If the switch arm drops, indicating a discontinuance of coal supply to the hammermill, a signal is developed which is applied to the control console 25 for control purposes. Additionally, the signal cuases the immediate closure of the water solenoid 95 and the oil solenoid 94 to discontinue all application of oil and water to the coal.

From FIG. 1 it will be noted that an oil flow transducer 100a is positioned in the oil pipe 17 to provide a signal to the control for purposes of bulk density regulation. Within the control console this signal is utilized to control the addition of water to the pipe 16. To elaborate, as long as the control console is counting pulses in each cycle indicating a "normal" bulk density of from 43 to 53 pounds per cubic foot, for example, the system operates to ensure that oil flow is within a desired range. Specifically, if the rate of oil addition to the coal exceeds an upper limit, the water rate is decreased. If the oil rate is below a lower limit, on the other hand, the water rate is increased. In this fashion, the rate of oil addition is taken as a primary control which is to be established within a certain desired range. The rate of water addition is either increased or decreased, as the case may be, when the oil rate is outside the desired range so as to bring the oil rate within the desired range. Otherwise, the water and oil rates are both varied in each counting cycle so that they are increased or decreased depending upon the variation of bulk density within the "normal" range of 43 to 53 pounds per cubic foot, for example, as described above.

In this regard, oil has been taken as the primary control, as just noted. However, water could be taken as the primary control just as easily, with oil varied to maintain the rate of water addition within a predetermined desirable range. Oil has been taken as the primary control since coal typically includes quantities of water and typically is of too low a bulk density, requiring the addition of oil to raise the bulk density into a desired range.

SIMULATING THE FALL OF COAL IN A COKE OVEN

As explained above, the conveyor 13 is adjustable in height over the conveyor 15 (FIG. 1) so as to provide a drop of coal just prior to the determination of bulk density that simulates the drop in an oven. In this fashion, the coal is provided to the radiation source in a bulk density condition the same as that existing in the oven. This procedure is necessary to ensure correct bulk density control. Oftentimes it is impossible, however, to provide a drop the same as that in a coke oven, since the drop might be too great for a conveying system at a particular mill. The present invention contemplates two drop simulating techniques. Apparatus for carrying out the first type of simulation is shown in FIGS. 2 to 4 and comprises a sled assembly 150 formed from a plurality of individual sleds 152. Six of such sleds are shown positioned across the conveyor 15, although this number is arbitrary. Each sled is carried by rods 154 pivotally secured thereto. The rods 154 are pivotally supported by support members 156 extending across and over the conveyor. The sleds 152 may have weights 158 positioned thereon. As shown in FIG. 3, the heights of the sleds 152 above the conveyor 15 may vary so that, in effect, the sled assembly assumes a general arcuate shape over the conveyor as viewed in a direction in line with the movement of the granular material on the conveyor.

The sled assembly as carried in the support members 156 is free to pivot in an arc generally in line with the movement of the granualr material on the conveyor (see FIG. 4). The individual sleds of the sled assembly pivot in arcs and, in their engagement with the coal, cause the bulk density to be changed to simulate the drop of the coal in the coke ovens and the accompanying change in bulk density that takes place there.

Figure 5:
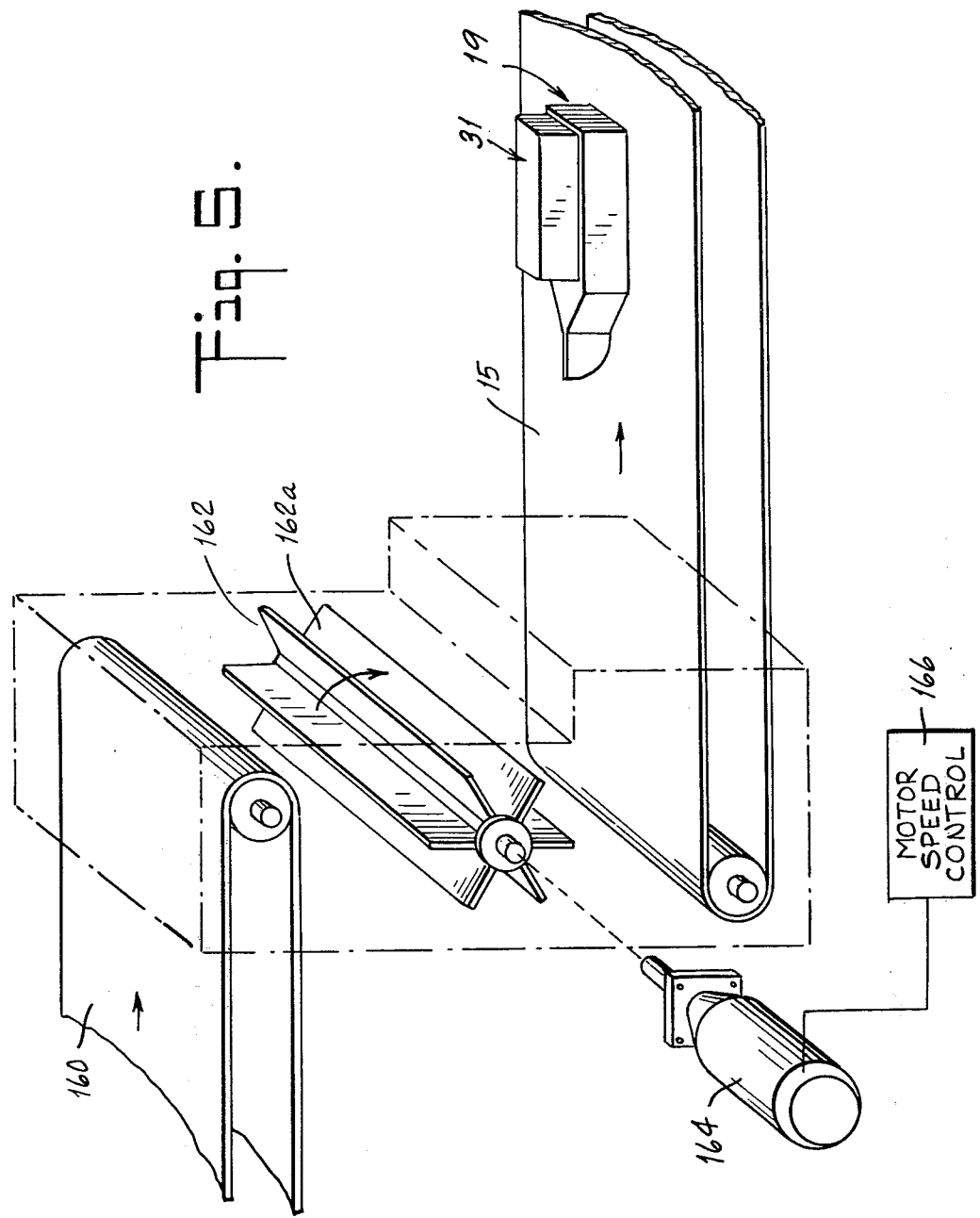
FIG. 5 is a perspective view of a paddle-wheel assembly in accordance with the invention for varying the bulk density of coal to simulate a drop in a oven.

An alternative scheme is shown in FIG. 5 in which a conveyor 160 conveys coal which is dropped to conveyor 15 that takes the material to the plow 19. In this case the crop between the conveyors 160 and 15 is not the same as the drop in the ovens to which the material is supplied. Accordingly, a paddle-wheel assembly 162 is positioned between the conveyors driven by a motor 164 under control of a motor speed control 166. The paddle-wheel assembly rotates, as shown by the arrow in FIG. 5, and blades 162a of the assembly strike the coal as it falls from the conveyor 160 onto the conveyor 15. The speed of rotation of the paddle-wheel assembly and the impact provided to the falling coal by the paddle-wheel blades is varied until the appropriate simulation of the bulk density change produced by the drop at the coke ovens is achieved.

While the novel features of the invention has been illustrated and decribed in connection with presently preferred embodiments, it is evident that these embodiments will enable others skilled in the art to apply the principles of the invention in forms departing from exemplary embodiments herein, and such departures are contemplated by the claims.

We claim:
1. A system for detecting the bulk density of coal supplied to an oven, wherein the coal is dropped into the oven, comprising means for providing a moving stream of coal to a detecting station which detects the bulk density of the coal passing through the station and thence to the oven, and means adjustably positioned before the detecting station for conditioning the coal so that it is in substantially the same bulk density condition in the detecting station as it is when dropped into the oven.

2. Apparatus as defined in claim 1, wherein the conditioning means includes means for dropping the coal by an adjustable distance substantially the same as the drop into the oven to which the coal is supplied.

3. Apparatus as defined in claim 1, wherein the conditioning means includes means for dropping the granular material from one location to another, and paddle-wheel means for striking the granular material as it is so dropped.

4. A system for detecting the bulk density of coal supplied to an oven, wherein the coal is dropped into the oven, comprising means for providing a moving stream of coal to a detecting station which detects the bulk density of the coal passing through the station and thence to the oven, and means positioned before the detecting station for conditioning the coal so that it is in substantially the same bulk density condition in the detecting station as it is when dropped into the oven, wherein the conditioning means comprises a sled assembly pivotable to swing in an arc generally in line with the movement of the material through the detecting station for bearing against the material before it passes through the station.

5. Apparatus as defined in claim 4, wherein the sled assembly comprises a plurality of sleds carrying weights thereon.

6. In a method of detecting the bulk density of coal supplied to a bulk density detecting station at which station the bulk density of the coal is detected and from which station the coal is subsequently supplied to an oven, wherein the coal is dropped into the oven, the step comprising conditoning the coal prior to its application to the detecting station so as to be substantially in the same bulk density condition in the detecting station as it is when dropped into the oven.

7. A method as defined in claim 6, wherein the coal is conditioned by being dropped a distance substantially the same as the drop into the oven to which the coal is supplied.

8. A method as defined in claim 6, wherein the coal is conditioned by being tamped prior to its application to the detecting station.

9. A method as defined in claim 6, wherein the coal is conditioned by being dropped from one location to another before it is applied to the detecting station, and struck as it is so dropped.

* * * * *